United States Patent [19]

Vigh

[11] Patent Number: 5,451,398
[45] Date of Patent: Sep. 19, 1995

[54] OPHTHALMIC AND DISINFECTING COMPOSITIONS AND METHODS FOR PRESERVING AND USING SAME

[75] Inventor: Joseph E. Vigh, Placentia, Calif.

[73] Assignee: Allergan, Inc., Irvine, Calif.

[21] Appl. No.: 174,485

[22] Filed: Dec. 27, 1993

Related U.S. Application Data

[63] Continuation-in-part of Ser. No. 912,862, Jul. 13, 1992, Pat. No. 5,277,901, which is a continuation-in-part of Ser. No. 461,181, Jan. 5, 1990, Pat. No. 5,145,643, and a continuation-in-part of Ser. No. 461,161, Jan. 5, 1990, Pat. No. 5,171,526.

[51] Int. Cl.$^6$ .............. A61K 31/74; A61K 31/425; A61K 31/14
[52] U.S. Cl. .............. 424/78.04; 514/367; 514/642; 514/912
[58] Field of Search .............. 514/642, 367, 912; 424/78.04

[56] References Cited

U.S. PATENT DOCUMENTS

| Re. 32,672 | 5/1988 | Huth et al. | 252/95 |
|---|---|---|---|
| 3,520,976 | 7/1970 | Buckman et al. | 424/270 |
| 3,771,989 | 11/1973 | Pera et al. | 514/642 |
| 3,874,870 | 4/1975 | Green et al. | 71/67 |
| 3,910,296 | 10/1975 | Karageozian et al. | 134/2 |
| 3,912,451 | 10/1975 | Gaglia, Jr. | 422/30 |
| 4,025,617 | 5/1977 | Green et al. | 514/642 |
| 4,029,817 | 6/1977 | Blanco et al. | 424/329 |
| 4,168,112 | 9/1979 | Ellis et al. | 351/160 |
| 4,250,269 | 2/1981 | Buckman et al. | 524/236 |
| 4,285,765 | 8/1981 | Pera et al. | 162/161 |
| 4,293,559 | 10/1981 | Buckman et al. | 424/270 |
| 4,304,894 | 12/1981 | Andrews et al. | 526/310 |
| 4,443,429 | 3/1984 | Smith et al. | 424/78 |
| 4,499,077 | 2/1985 | Stockel et al. | 424/661 |
| 4,525,346 | 6/1985 | Stark | 514/642 |
| 4,532,128 | 7/1985 | Sheldon et al. | 424/78 |
| 4,568,517 | 2/1986 | Kaspar et al. | 422/30 |
| 4,615,882 | 10/1986 | Stockel | 424/80 |
| 4,654,208 | 3/1987 | Stockel et al. | 514/642 |
| 4,783,483 | 11/1988 | Ogunbiyi et al. | 514/635 |
| 4,786,436 | 11/1988 | Ogunbiyi et al. | 252/352 |
| 4,836,986 | 6/1989 | Ogunbiyi et al. | 422/28 |
| 4,839,373 | 6/1989 | Ito et al. | 514/367 |
| 4,866,080 | 9/1989 | Hollis et al. | 514/367 |
| 4,866,081 | 9/1989 | Ito et al. | 514/367 |
| 4,908,209 | 3/1990 | McIntosh, Jr. et al. | 424/78 |
| 4,935,232 | 6/1990 | McIntosh | 424/78 |
| 4,983,618 | 1/1991 | Pulido et al. | 514/367 |
| 5,073,638 | 12/1991 | Conaway et al. | 548/169 |
| 5,145,643 | 9/1992 | Dziabo et al. | 514/642 |
| 5,171,526 | 12/1992 | Wong et al. | 422/28 |
| 5,196,443 | 3/1993 | Oppong et al. | 514/367 |
| 5,198,440 | 3/1993 | Oppong et al. | 514/241 |

FOREIGN PATENT DOCUMENTS

| 0296441 | 6/1988 | European Pat. Off. |
| 63-131124 | 4/1988 | Japan |
| 2139260 | 11/1984 | United Kingdom |

OTHER PUBLICATIONS

Toxicity Profile TCMTB, Mar. 1992 Buckman Laboratories, Inc. Material Safety Data Sheet Revised Mar. 30, 1992 TCMTB Analytical Standard.
The Buckman Toxicity Profile Jul. 25, 1984.
The Buckman Technical Specifications Sep. 23, 1981.
Buckman Laboratories, Inc. 1256 N. McLean Memphis, Tenn. 38108.
The Buckman Material Safety Data Sheet Aug. 13, 1984.
Buckman Laboratories, Inc. 1256 N. McLean Blvd. Memphis, Tenn. Feb. 18, 1993.
The Lens Care Research Bulletin Bausch and Lomb SL-7497, Jan. 1974.
The Croda, Inc. Bulletin-Crodnoel Q (L,M&S) Jun. 24, 1986. Croda, Inc. 183 Madison Ave. New York N.Y. 10016
The Croda, Inc. Bulletin-Croquat L Oct. 16, 1982 Croda, Inc. 183 Madison Ave. New York, N.Y. 10016.
The Croda, Inc. Material Safety Data Sheet (lauroyl quaternizec hydroxyethyl cellulose) Jan. 22, 1987.
The Croda, Inc. Material Safety Data Sheet (cocyl quaternized hydroxyethyl cellulose) Jan. 22, 1987.
The Croda, Inc. Material Safety Data Sheet (stearoyl quaternized hydroxyethyl cellulose) Jan. 22, 1987 Croda, Inc. 183 Madison Ave. N.Y. 10016.

*Primary Examiner*—Zohreh Fay
*Attorney, Agent, or Firm*—Frank J. Uxa

[57] ABSTRACT

Ophthalmic compositions, such as those used to care for contact lenses, methods of preserving such compositions, and methods for disinfecting contact lenses using certain of such compositions are disclosed. The compositions may comprise an ophthalmically acceptable, liquid aqueous medium and, included therein, an effective preserving or disinfecting amount of a combination of certain oxygen-containing ionene polymers and one or more antimicrobial thiocyano components.

22 Claims, No Drawings

OPHTHALMIC AND DISINFECTING COMPOSITIONS AND METHODS FOR PRESERVING AND USING SAME

RELATED APPLICATIONS

This application is a continuation-in-part of copending application Ser. No. 912,862, filed Jul. 13, 1992 now U.S. Pat. No. 5,277,901, which, in turn, is a continuation-in-part of applications Ser. No. 461,181, filed Jan. 5, 1990, now U.S. Pat. No. 5,145,643 and Ser. No. 461,161, filed Jan. 5, 1990, now U.S. Pat. No. 5,171,526. The disclosure of each of the above-noted application and patents is hereby incorporated in its entirety by reference herein.

BACKGROUND OF THE INVENTION

This invention relates to ophthalmic compositions and methods for preserving and using such compositions. More particularly, the present invention relates to ophthalmic compositions, e.g., useful in caring for contact lenses, which include one or more of certain ionene polymers as preservatives or disinfectants, and to methods for disinfecting and/or preserving using such compositions.

Various compositions, e.g., solutions, are used in association with contact lenses to ensure that the lenses may be safely, comfortably and conveniently worn. Contact lens care compositions, for example, disinfecting compositions, preserving compositions, cleaning compositions, wetting compositions, conditioning compositions and the like, often utilize at least one disinfectant or preservative, depending on the type of composition, for disinfecting or preserving contact lenses after wear or preserving the lens care composition itself. A contact lens disinfecting composition generally has sufficient antimicrobial activity so that when the composition is contacted with a lens to be disinfected, microorganisms associated with the lens are killed or otherwise removed and the contact lens is effectively disinfected within a reasonable time, e.g., in the range of about 0.1 hour to about 12 hours. A contact lens disinfecting composition may be termed a microbicidal composition. In contrast, a contact lens preserving composition has sufficient antimicrobial activity, often less of such activity than is present in a contact lens disinfecting composition, so that when the composition is contacted with a contact lens substantially no increase in the microorganism population in the composition is obtained. A contact lens preserving composition may be termed a microbiostatic composition or a microbicidal composition. Contact lens care compositions are preserved to prevent any substantial increase in the population of contaminating microorganisms in the compositions and, thereby, to extend their shelf life. Such preserved contact lens care compositions may be termed microbiostatic compositions. Some preservatives used in lens preserving compositions or in preserved compositions may also be used as disinfecting agents in lens disinfecting compositions.

Various compounds are known for use as preserving agents in contacts lens preserving compositions and preserved contact lens care compositions. Examples include thimerosal, benzalkonium chloride and chlorhexidine. However, these preserving agents are known to exhibit ocular toxicity which may result in irritation or sensitivity to the eye. The degree of ocular toxicity increases when these agents are utilized as disinfecting agents. Further, a soft contact lens, a rigid gas permeable contact lens (RGP) or a hard contact lens can absorb or adsorb these compounds. This causes the contact lens to retain the irritating compound and contributes to the eye irritation and sensitivity which may result.

Stark U.S. Pat. No. 4,525,346 discloses a contact lens disinfecting solution and preserved contact lens care compositions containing 1-tris (2-hydroxyethyl) ammonium-2-butenyl-4-poly [1-dimethyl ammonium-2-butenyl]-w-tris (2-hydroxyethyl-) ammonium the salt of which has a pharmaceutically acceptable anion. The quaternary ammonium polymer disclosed in this Stark patent is capable of causing irritation and sensitivity to some contact lens wearers.

Japanese Patent Publication 63131124 discloses a liquid composition for contact lens care including as an antimicrobial component a polymeric condensate of a diamine, such as N,N,N',N'-tetramethyl 1,2-diaminoethane, and a dihalogen compound, such as 1,2-dichloroethane. Such polymeric condensates include no oxygen. Further, there is no suggestion that other polymeric condensates are useful as antimicrobial agents in the contact lens care context.

Other conventional methods of contact lens chemical disinfection utilize one or more active disinfecting agents in an aqueous medium, for example a chlorhexidine/thimerosal solution or a relatively mild solution of hydrogen peroxide. Some of these disinfecting solutions, such as those named above, are cytotoxic and are known to be adsorbed or absorbed onto or into a contact lens and cause the lens to elicit a cytotoxic response after disinfection. For example, contact lenses which have been soaked in a disinfecting hydrogen peroxide solution are to be treated to remove residual hydrogen peroxide, e.g., by soaking in a catalase solution, before they may be comfortably and safely worn again. If residual hydrogen peroxide remains on the lenses, then irritation or injury to the eye may result. A lens disinfecting system employing a substantially nonoxidative disinfectant composition is particularly useful since the risk of introducing active oxidizing agents into the eye is substantially eliminated.

Ellis et al U.S. Pat. No. 4,168,112 discloses treating an ionically charged contact lens with a lens solution containing an oppositely charged ionic polymer to form a hydrophilic polyelectrolyte complex on the lens surface. This complex forms a hydrogel and acts as a cushion which provides comfort to the eye. Ionene polymers are among the many ionic polymers disclosed by Ellis et al. In addition, Ellis et al discloses that other additives, such as preservatives, e.g., benzalkonium chloride, ethylenediaminetetraacetic acid, mercurials and chlorobutanol, can be included in the lens treating solutions. Ellis et al does not distinguish between ionene polymers, nor is there any suggestion than any ionene polymers are useful as preservatives or disinfectants in the contact lens care context.

Stockel et al U.S. Pat. No. 4,499,077 discloses oxidative contact lens disinfecting compositions including stabilized chlorine dioxide and a quaternary ammonium compound which is a copolymer of at least one mono- or di-tertiary amine and a dihalo organic compound. Stockel U.S. Pat. No. 4,654,208 discloses oxidative contact lens disinfecting compositions including one or more of the quaternary ammonium copolymers noted above in this paragraph plus a potentiating amount of an oxidizing agent. Neither of the Stockel et al patents disclose non-oxidative contact lens care compositions using such quaternary ammonium copolymers.

A number of patents have disclosed the use of 2-(thiocyanomethylthio)benzothiazole, alone or in combination with various other materials, as having antimicrobial activity in metalworking fluids (Hollis et al U.S. Pat. No. 5,198,440 and Hollis et al U.S. Pat. No. 5,196,443); as microbicidal preservatives for dyes, pastes, lumber, leather, textiles, pulp and industrial raw materials (Ito U.S. Pat. No. 4,866,081 and Ito et al U.S. Pat. No. 4,839,373); to control fouling by marine and fresh water mollusks (Hollis et al U.S. Pat. No. 4,866,080); and to inhibit growth of microorganisms in water used for industrial purposes (Buckman et al U.S. Pat. No. 4,293,559, Johnson et al U.S. Pat. No. 4,285,765 and Buckman et al U.S. Pat. No. 3,520,976). None of these patents, nor any known prior art, teach or suggest the use of benzothiazole derivatives in contact lens care compositions or in ophthalmic compositions. In fact, as noted above, benzothiazole derivatives have been suggested for use in heavy industrial applications which tends to lead away from using such materials in applications involving the eye, one of the most sensitive organs of the body.

In general, it is advantageous to reduce the amount of disinfectant and/or preservative used in the contact lens care context. For example, with reduced amounts of such materials present, adverse reactions to the compositions are reduced. Also, the cost of obtaining effective contact lens disinfection and preserved ophthalmic compositions is reduced.

Thus, it is readily apparent that a continuing need exists for safe and efficacious compositions that can be used as contact lens disinfecting and preserving compositions and as preserved contact lens care compositions.

SUMMARY OF THE INVENTION

New disinfecting and preserving compositions and methods, particularly such compositions and methods directed to contact lens care, have been discovered. The present compositions include effective disinfectants and/or preservatives and are preferably substantially non-oxidative. Thus, for example, a contact lens can be effectively disinfected in a reasonable length of time. Also, contact lens care products can be effectively preserved against growth of contaminating microorganisms. Importantly, such disinfecting and preserving activities are achieved and the contact lenses disinfected, preserved or otherwise cared for using the present compositions can be safely and comfortably worn with little or no risk of eye irritation or sensitivity, e.g., from the presence of residual oxidizing agent.

In one broad aspect of the invention, compositions, preferably substantially non-oxidative compositions, useful for disinfecting a contact lens are provided. Preserved compositions, preferably substantially nonoxidative preserved compositions, are also provided. These compositions include an ophthalmically acceptable, preferably sterile, medium, preferably a liquid aqueous medium. Included within this medium is an effective disinfecting, or preserving, amount of a combination of (1) an ophthalmically acceptable, quaternary ammonium polymer selected from ionene polymers containing an oxygen atom covalently bonded to two carbon atoms and mixtures thereof, and (2) an antimicrobial component selected from thiocyano components and mixtures thereof. In a particularly useful embodiment, the thiocyano component is selected from thiocyanothiazoles, more preferably thiocyanobenzothiazoles and especially 2(thiocyanomethylthio) benzothiazole, derivatives thereof and mixtures thereof. Methods of disinfecting a contact lens include contacting the lens to be disinfected with an appropriate composition, as described herein.

Such combinations of quaternary ammonium polymers and thiocyano components have surprisingly been found to be effective disinfectants and preservatives in the contact lens care context, preferably without the need for oxidizing agents. With the presently useful combinations being employed, effective disinfection and preservation is achieved, preferably with reduced concentrations of quaternary ammonium polymers and thiocyano components being used relative to compositions in which only one of these materials is used as the sole disinfectant or preservative. Contact lenses which are disinfected, or otherwise treated using the present compositions, can be safely and comfortably worn with little or no risk of eye irritation or sensitivity.

Preserved compositions, e.g., contact lens care compositions, which include an ophthalmically acceptable medium, preferably containing one or more components effective to beneficially affect a contact lens and/or the wearing of a contact lens, are included within the scope of the present invention. Such preserved compositions include an effective preserving amount of a combination of quaternary ammonium polymers and thiocyano components, as described herein, and preferably are substantially non-oxidative.

DETAILED DESCRIPTION OF THE INVENTION

The present invention is applicable to disinfecting all types of lenses, e.g., contact lenses, which are benefitted by such disinfecting. Such lenses, e.g., conventional soft contact lenses, RGPs and hard contact lenses, may be made of any suitable material or combination of materials and may have any suitable configuration. The invention is also applicable to preserving compositions, such as contact lens care compositions, and other eye care products which are benefitted by being preserved.

One important feature of the compositions of the present invention is the inclusion of an effective, e.g., for disinfecting and/or preserving, amount of a combination of (1) at least one ophthalmically acceptable, quaternary ammonium polymer selected from the group consisting of ionene polymers containing an oxygen atom covalently bonded to two carbon atoms, hereinafter referred to as "(C—O—C) ionene polymers", and mixtures thereof, and (2) a thiocyano component, preferably selected from ophthalmically acceptable thiocyanothiazoles, more preferably selected from thiocyanobenzothiazoles, derivatives thereof and mixtures thereof. Without wishing to limit the invention to any particular theory of operation, it is believed that the combinations useful in the present invention are sufficiently active to provide the desired degree of disinfecting or preserving without causing substantial eye irritation or sensitivity.

The presently useful quaternary ammonium polymers are distinguished from the quaternary ammonium polymer described in Stark U.S. Pat. No. 4,525,346 and the polymeric condensate described in Japanese Patent Publication 63131124. In the Stark patent and the Japanese Publication, the quaternary ammonium polymer and the polymeric condensate are not (C—O—C) ionene polymers. The presently useful quaternary ammonium polymers provide the desired antimicrobial activity without causing substantial eye irritation and sensitivity.

The presently useful quaternary ammonium polymers preferably have the following repeating units:

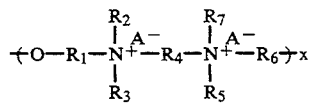

wherein $R_1$, $R_4$ and $R_6$ are each independently selected from alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from ophthalmically acceptable anions, and x is the number of repeating units in the polymer and is an integer in the range of about 5 to about 30. A particularly useful quaternary ammonium polymer has the following repeating units

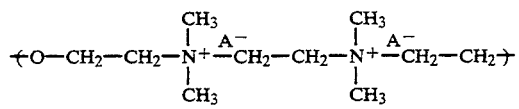

The number of repeating units per polymer molecule, represented by x, is more preferably about 8 to about 30, especially about 14.

Examples of ophthalmically acceptable anions include chloride ($Cl^-$), bromide, iodide, bisulfate, phosphate, acid phosphate, nitrate, acetate, maleate, fumarate, oxalate, lactate, tartrate, citrate, gluconate, saccharate, p-toluene sulfonate and the like. The preferred ophthalmically acceptable anion is $Cl^-$.

In one particularly useful embodiment, the quaternary ammonium polymer has a molecular weight in the range of about 500 to about 5000.

Methods for producing the presently useful quaternary ammonium polymers are described in Buckman et al U.S. Pat. No. 4,250,269, which patent is hereby incorporated in its entirety herein by reference. A specific example of a quaternary ammonium polymer useful in the present invention is poly (oxyethylene (dimethyliminio) ethylene (dimethyliminio) ethylene dichloride), such as that sold by Buckman Laboratories, Inc. under the trademark WSCP.

The presently useful thiocyano components are antimicrobial. That is, such materials are effective to kill one or more microorganisms and/or to prevent population increase of one or more microorganisms at the concentrations of such materials employed. As used herein, the term "thiocyano component" refers to those compounds which include a thiocyano group, that is a—S—C≡N group. The thiocyano component is preferably selected from thiocyanothiazoles, more preferably from thiocyanobenzothiazoles, derivatives thereof and mixtures thereof. The thiocyano components are preferably ophthalmically acceptable in the concentrations in which they are employed. The thiocyano components, in combination with the presently useful quaternary ammonium polymers, should have sufficient antimicrobial activity to provide for the desired disinfecting and/or preserving.

Especially useful thiocyano components for use in the present invention include 2(thiocyanomethylthio)benzothiazole, derivatives thereof and mixtures thereof. Commercially available thiocyano components useful in the present invention include 2(thiocyanomethylthio)benzothiazole sold by Buckman Laboratories, Inc. under the trademark TCMTB. The presently useful thiocyano components can be made by various processes. For example, as described in Conaway et al U.S. Pat. No. 5,073,638, a chloro derivative, such as 2-chloromethylthiobenzothiazole, can be reacted, in the presence of a glycol ether solvent, with either an alkali metal or an ammonium thiocyanate at a temperature and for a time sufficient to produce the thiocyano component, such as 2-(thiocyanomethylthio)benzothiazole. The disclosure of Conaway et al U.S. Pat. No. 5,073,638 is hereby incorporated in its entirety by reference herein.

The presently useful quaternary ammonium polymers and thiocyano components are preferably dispersable or soluble in the ophthalmically acceptable medium. Since contact lens disinfecting, preserving and other care compositions are most often solutions, the quaternary ammonium polymers and benzothiozole components are more preferably soluble in the medium. The amount of quaternary ammonium polymers and thiocyano components employed in the present compositions is that sufficient to effect the desired result. Care should be taken to avoid excessive amounts of quaternary ammonium polymers and thiocyano components. Not only are such materials quite expensive, but the use of large excesses may result in some degree of eye irritation and/or sensitivity. The presently useful quaternary ammonium polymer and thiocyano component, each is preferably present in an amount in the range of about 0.00001% to about 1%, more preferably about 0.0001% to about 0.5%, by weight per volume of ophthalmically acceptable medium.

Ophthalmically acceptable salts may include one or more ophthalmically acceptable anions, e.g., as noted above, or ophthalmically acceptable cations, in particular alkali and alkali metal cations. Materials which provide more than one beneficial or desired property to the present compositions may also be included. For example, certain combinations of quaternary ammonium compounds which possess both antimicrobial activity and wetting properties may be included. Each of these agents/materials may be included in the present compositions in an amount effective to provide the beneficial or desired property or properties. The compositions of the present invention include an ophthalmically acceptable medium, preferably an ophthalmically acceptable liquid aqueous medium. This medium often acts as a carrier, e.g., as a solvent, for the other components in the composition. A material is "ophthalmically acceptable" if the material can be placed into a mammalian eye without causing any substantial damage or harm to the eye. One particularly useful ophthalmically acceptable medium is water. Preferably, the medium, and in fact the entire composition, is sterile.

One or more additional components can be included in the present compositions based on the particular application for which the compositions are formulated. Thus, the present compositions can be formulated as disinfecting compositions, cleaning compositions, wetting compositions, conditioning compositions, soaking compositions and the like. Also, the present compositions can be formulated to be useful in performing two or more contact lens caring operations. For example, a disinfecting/cleaning composition, or a cleaning/conditioning composition or even an all purpose lens care composition can be formulated and such multifunctional compositions are included within the scope of the present invention.

The additional component or components included in the present compositions are chosen to impart or provide at least one beneficial or desired property to the compositions. Such additional components may be selected from components which are conventionally used in one or more contact lens care compositions. Examples of such additional components include buffering agents, cleaning agents, wetting agents, surfactants, nutrient agents, sequestering agents, viscosity builders, tonicity agents, contact lens conditioning agents, antioxidants, pH adjustors, and the like. These additional components are each included in the present compositions in an amount effective to impart or provide the beneficial or desired property to the compositions. For example, such additional components may be included in the present compositions in amounts similar to the amounts of such components used in other, e.g., conventional, contact lens care products.

Useful buffering agents include, but not limited to, acetate buffers, citrate buffers, phosphate buffers and borate buffers. Acids and bases may be used to adjust the pH of the present compositions as needed. Preferably, the present compositions have ophthalmically acceptably pHs.

Useful wetting agents include, but are not limited to, polyvinyl alcohol, poloxamers, polyvinyl pyrrollidone, hydroxypropylmethyl cellulose and mixtures thereof.

Useful sequestering agents include, but are not limited to, disodium ethylene diamine tetraacetate, alkali metal hexametaphosphate, citric acid, sodium citrate and mixtures thereof.

Useful tonicity adjustors include, but are not limited to, sodium chloride, potassium chloride, mannitol, dextrose, glycerin, propylene glycol and mixtures thereof.

Useful viscosity builders include, but are not limited to, hydroxyethyl cellulose, hydroxy methyl cellulose, polyvinyl pyrrolidone, hydroxypropylmethyl cellulose, polyvinyl alcohol and mixtures thereof.

Useful antioxidants include, but are not limited to, sodium metabisulfite, sodium thiosulfate, N-acetylcysteine, butylated hydroxyanisole, butylated hydroxytoluene and mixtures thereof.

Certain of the presently useful thiocyano components have quite limited water solubility. If, as is preferred, the final product in accordance with the present invention is to be a solution, a surfactant component in an amount effective to enhance the solubility of the thiocyano component in the composition or liquid aqueous medium included in the composition is preferably included. A suitable surfactant may be employed provided that it is effective to provide the desired enhanced solubility. One particularly useful class of surfactants are the ethylene oxide/propylene oxide block polymers, many of which are commercially available and are compatible with, or substantially nontoxic to, ocular tissue. Specific examples include ethylene oxide/propylene oxide block copolymers, sold by BASF under the trademark Pluronic P-85 and Pluronic P-104. The surfactant component is preferably present in an amount in the range of about 0.1% to about 3% (w/v) of the composition.

In a particularly useful embodiment, the quaternary ammonium polymer/thiocyano component-containing compositions further include at least one enzyme effective to remove debris from a contact lens. Among the types of debris that form on a contact lens during normal use are protein-based debris, mucin-based debris, lipid-based debris and carbohydrate-based debris. One or more types of debris may be present on a single contact lens.

The enzyme employed may be selected from enzymes which are conventionally employed in the enzymatic cleaning of contact lenses. For example, many of the enzymes disclosed in Huth et al U.S. Pat. No. RE 32,672 and Karageozian et al U.S. Pat. No. 3,910,296 are useful in the present invention. Each of these patents is incorporated in its entirety by reference herein. Among the useful enzymes are those selected from proteolytic enzymes, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus, II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two sub-classes, subtilisin A and subtilisin B. In the subtilisin A grouping are enzymes derived from such species as *B. subtilis, B. licheniformis* and *B. pumilis.* Organisms in this sub-class produce little or no neutral protease or amylase. The subtilisin B sub-class is made up of enzymes from such organisms as *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillopeptidase A and B, pronase E (from *S. griseus*) and dispase (from *B. polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the excipient it contains.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent. Thus, for any given enzyme, there is a particular pH range in which that enzyme will function best. The determination of such range can readily be done by known techniques.

The present compositions may be used in the care of a contact lens, e.g., to disinfect the lens, to otherwise treat the lens and/or to make wearing the lens safe and comfortable. The present compositions, formulated appropriately, may be used in conventional contact lens care regimens by using the present compositions in place of prior conventional compositions. In many instances, these contact lens care regimens involve contacting the lens with the present composition in an amount, and at conditions, effective to obtain the beneficial or desired contact lens care result. For example, a contact lens to be disinfected may be contacted with a disinfecting composition, e.g., aqueous solution, according to the present invention, preferably at a temperature in the range of about 0° C. to about 100° C., more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time to substantially disinfect the lens being treated. Such contacting times can be in the range of about 1 minute to about 12 hours or more.

After this contacting, the disinfected contact lens can be taken from the composition and placed directly in an eye, e.g., a human eye, for safe and comfortable wear. Alternately, after being disinfected, the contact lens can be contacted with a second medium, e.g., a liquid aqueous medium such as a preserved isotonic saline solution, prior to being placed in the eye of the wearer of the disinfected contact lens.

The contact lens care compositions disclosed herein are adaptable for use in most types of contact lens care equipment, such as ultrasonic cleaners and the like.

The following examples are set out to illustrate, but not limit, the scope of this invention.

EXAMPLES 1 TO 5

A series of five (5) compositions were prepared by blending the constituents together. Each of the compositions included the following:

|  | % (w/v) |
|---|---|
| Boric acid | 0.4 |
| Sodium borate | 0.2 |
| Sodium chloride | 0.6 |
| Hydoxyethyl cellulose | 0.4 |
| Surfactant[1] | 0.5 |
| Purified water, USP | QS |

[1]A mixture containing ethylene oxide/propylene oxide block copolymer sold under the trademark Pluronic P-85 by BASF.

One or more additional components were included in each of these compositions as follows:

| Constituent | Composition | | | | |
|---|---|---|---|---|---|
|  | 1 (control) | 2 | 3 | 4 | 5 |
| Ionene polymer concentrate, % (w/v)[2] | 0.006 | 0.006 | 0.006 | 0.006 | 0.006 |
| TCMTB, % (w/v)[3] | — | 0.01 | 0.013 | 0.013 | 0.016 |
| Sebacic acid, % (w/v) | — | — | — | 0.5 | — |

[2]A concentrate containing 60% by weight of poly (oxyethylene(dimethylimini-o)ethylene (dimethyliminio) ethylene dichloride) sold under the trademark WSCP by Buckman Laboratories, Inc.
[3]2-(thiocyanomethylthio)benzothiazole sold under the trademark TCMTB by Buckman Laboratories, Inc.

Each of these compositions was tested for antimicrobial activity against a series of five (5) microrganisms using conventional testing techniques.

The log-drops in microorganism population, expressed in CFU/ml, at the six (6) hour time point for each of these compositions against each of the microorganisms was as follows:

| Microorganis (Inoculum size) | Composition | | | | |
|---|---|---|---|---|---|
|  | 1 | 2 | 3 | 4 | 5 |
| S. marcescens ($3.0 \times 10^6$) | 1.0 | 0.8 | 0.8 | 0.5 | 0.7 |
| S. aureus ($1.5 \times 10^6$) | 1.8 | 1.8 | 1.6 | 1.4 | 1.7 |
| P. aeruginosa ($2.0 \times 10^6$) | Total Kill | Total Kill | 5.3 | 3.7 | Total Kill |
| C. albicans ($9.0 \times 10^5$) | No Kill | 4.0 | 4.0 | 4.0 | 4.0 |
| A. fumigatus ($4.0 \times 10^5$) | No Kill | 1.3 | 1.3 | 1.1 | 1.3 |

These results indicate that the compositions according to the present invention, that is Compositions 2, 3, 4 and 5, which contain a combination of ionene polymer and thiocyano component are effective as contact lens disinfectants. In addition, these results indicate that the above-noted combination of antimicrobial components is useful as a preservative in ophthalmic products, such as contact lens care products. In particular, the results illustrate that the present compositions are more effective against C. albicans and A. fumigatus relative to Composition 1, which includes no thiocyano component. With regard to Composition 4, sebacic acid is shown to have a very slight negative effect on all the test microorganisms.

EXAMPLE 6

A contact lens disinfecting composition is prepared by blending the constituents together. This composition has the following composition:

| Constituent | Concentration, % (w/v) |
|---|---|
| Boric acid | 0.6 |
| Sodium borate | 0.15 |
| Disodium ethylene diamine tetraacetate | 0.75 |
| Sodium chloride | 0.35 |
| Surfactant[4] | 1.25 |
| Hydroxyethyl cellulose | 0.4 |
| Ionene polymer concentrate[4] | 0.005 |
| TCMTB[4] | 0.010 |

[4]As described in Example 1 to 5

EXAMPLE 7

The composition of Example 6, i.e., Composition 6, is used to disinfect a conventional rigid gas permeable (RGP) contact lens as follows. 7.5 ml of the composition is provided at room temperature. The contact lens to be disinfected is placed in the composition. Four (4) hours after the contact lens is first introduced into the composition, it is removed from the composition and placed directly into the wearer's eye. It is found that after four (4) hours, the contact lens is effectively disinfected. Also, the lens wearer experiences no discomfort or eye irritation from wearing the disinfected contact lens. Alternately, after the contacting for four (4) hours noted above, the disinfected contact lens is rinsed with preserved or non-preserved sterile isotonic saline solution prior to placing the disinfected lens in the wearer's eye. The lens wearer experiences no discomfort or eye irritation from wearing the disinfected contact lens.

EXAMPLE 8

Example 7 is repeated except that about 50 ppm by weight of subtilisin A, based on the total weight of the Composition 6 used, is added at the same time the contact lens to be disinfected is added to the composition. Four (4) hours after the contact lens is first introduced into the composition, it is removed from the composition, rinsed with Composition 6, or with preserved or non-preserved sterile isotonic saline solution, and placed directly into the wearer's eye. It is found that after four (4) hours, the contact lens is effectively disinfected and cleaned of protein-based debris. Also, the lens wearer experiences no discomfort or eye irritation from wearing the disinfected and cleaned contact lens.

While this invention has been described with respect to various specific examples and embodiments, it is to be understood that the invention is not limited thereto and that it can be variously practiced within the scope of the following claims.

What is claimed is:

1. A method for disinfecting a contact lens comprising:
    contacting a contact lens with a liquid medium which is ophthalmically acceptable and includes an effective disinfecting amount of a combination of (1) a quaternary ammonium polymer selected from the group consisting of ionene polymers containing an oxygen atom covalently bonded to two carbon atoms and mixtures thereof, and (2) an antimicrobial component selected from the group consisting of thiocyanobenzothiazoles, derivatives thereof and mixtures thereof at conditions to effectively disinfect said contact lens.

2. The method of claim 1 wherein said liquid medium is substantially non-oxidative and is a liquid aqueous medium.

3. The method of claim 1 wherein said antimicrobial component is selected from the group consisting of 2-(thiocyanomethylthio)benzothiazole, derivatives thereof and mixtures thereof.

4. The method of claim 1 which further comprises contacting said contact lens in a liquid medium with at least one enzyme capable of removing debris from a contact lens in an amount effective to remove debris from said contact lens.

5. The method of claim 1 wherein said quaternary ammonium polymer has a repeating unit

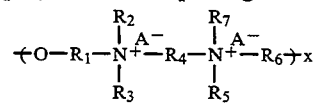

wherein $R_1$, $R_4$ and $R_6$ are each independently selected from the group consisting of alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from the group consisting of ophthalmically acceptable anions, and x is the number of said repeating units in said quaternary ammonium polymer and is an integer in the range of about 5 to about 30, and said composition further includes a surfactant component in an amount effective to enhance the solubility of said antimicrobial component in said liquid medium.

6. The method of claim 3 wherein said quaternary ammonium polymer is poly (oxyethylene (dimethyliminio) ethylene (dimethyliminio) ethylene dichloride) and said antimicrobial component is 2-(thiocyanomethylthio)benzothiaozle.

7. A method for preserving an ophthalmically acceptable medium comprising: contacting an ophthalmically acceptable medium with an effective preserving amount of a combination of (1) a quaternary ammonium polymer which is ophthalmically acceptable and is selected for the group consisting of ionene polymers containing an oxygen atom covalently bonded to two carbon atoms and mixtures thereof, and (2) an antimicrobial component selected from the group consisting of thiocyanobenzothiazoles, derivatives thereof and mixtures thereof and which is ophthalmically acceptable at conditions to form an effectively preserved ophthalmically acceptable medium including (1) and (2).

8. The method of claim 7 wherein said ophthalmically acceptable medium is a substantially non-oxidative, liquid aqueous medium.

9. The method of claim 7 wherein said antimicrobial component is selected from the group consisting of 2-(thiocyanomethylthio)benzothiazole, derivatives thereof and mixtures thereof.

10. The method of claim 7 wherein said quaternary ammonium polymer has a repeating unit

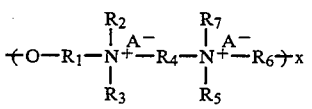

wherein $R_1$, $R_4$ and $R_6$ are each independently selected from the group consisting of alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from the group consisting of ophthalmically acceptable anions, and x is the number of said repeating units in said quaternary ammonium polymer and is an integer in the range of about 5 to about 30, said opthalmically acceptable medium further including a surfactant component in an amount effective to enhance the solubility of said antimicrobial component in said opthalmically acceptable medium.

11. The method of claim 9 wherein said quaternary ammonium polymer is poly (oxyethylene (dimethyliminio) ethylene (dimethyliminio) ethylene dichloride)

and said at least one other antimicrobial component is 2-(thiocyanomethylthio)benzothiazole.

12. A composition useful for disinfecting a contact lens comprising an ophthalmically acceptable, liquid aqueous medium and an effective disinfecting amount of a combination of (1) a quaternary ammonium polymer which is ophthalmically acceptable and is selected from the group consisting of ionene polymers containing an oxygen atom covalently bonded to two carbon atoms and mixtures thereof, and (2) an antimicrobial component selected from the group consisting of thiocyanobenzothiazoles, derivatives thereof and mixtures thereof.

13. The composition of claim 12 which is substantially non-oxidative and wherein each of said quaternary ammonium polymer and said antimicrobial component is present in an amount in the range of about 0.00001% to about 1% by weight per volume of said ophthalmically acceptable liquid aqueous medium.

14. The composition of claim 12 which further comprises at least one enzyme capable of removing debris from a contact lens in an amount effective to remove debris from a debris laden contact lens.

15. The composition of claim 12 wherein said quaternary ammonium polymer has a repeating unit

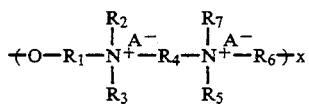

wherein $R_1$, $R_4$ and $R_6$ are each independently selected from the group consisting of alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from the group consisting of ophthalmically acceptable anions, and x is the number of said repeating units in said quaternary ammonium polymer and is an integer in the range of about 5 to about 30, and which further comprises a surfactant component in an effective amount to enhance the solubility of said antimicrobial component in said ophthalmically acceptable liquid aqueous medium.

16. The composition of claim 12 wherein said quaternary ammonium polymer is poly (oxyethylene (dimethyliminio) ethylene (dimethyliminio) ethylene dichloride) and said antimicrobial component is selected from the group consisting of 2(thiocyanomethylthio) benzothiazole, derivatives thereof and mixtures thereof.

17. The composition of claim 16 wherein said antimicrobial component is 2-(thiocyanomethylthio) benzothiazole.

18. A preserved composition comprising an ophthalmically acceptable medium including, an effective preserving amount of a combination of (1) a quaternary ammonium polymer which is ophthalmically acceptable and is selected from the group consisting of ionene polymers containing an oxygen atom covalently bonded to two carbon atoms and mixtures thereof, and (2) an antimicrobial component selected from the group consisting of thiocyanobenzothiazoles, derivatives thereof and mixtures thereof.

19. The composition of claim 18 wherein said preserved composition is substantially non-oxidative and said ophthalmically acceptable medium is a liquid aqueous medium.

20. The composition of claim 18 wherein said polymer quaternary ammonium polymer has a repeating unit

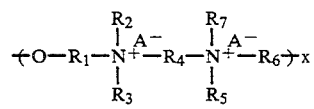

wherein $R_1$, $R_4$ and $R_6$ are each independently selected from the group consisting of alkylene radicals containing 1 to about 6 carbon atoms, $R_2$, $R_3$, $R_5$ and $R_7$ are each independently selected from alkyl radicals containing 1 to about 6 carbon atoms, each $A^-$ is independently selected from the group consisting of ophthalmically acceptable anions, and x is the number of said repeating units in said quaternary ammonium polymer and is an integer in the range of about 8 to about 30, and which further comprises a surfactant component in an amount effective to enhance the solubility of said antimicrobial component in said opthalmically acceptable medium.

21. The composition of claim 18 wherein said quaternary ammonium polymer is poly (oxyethylene (dimethyliminio) ethylene (dimethyliminio) ethylene dichloride) and said antimicrobial component is selected from the group consisting of 2-(thiocyanomethylthio)benzothiazole, derivatives thereof and mixtures thereof.

22. The composition of claim 21 wherein said antimicrobial component is 2-(thiocyanomethylthio) benzothiazole.

* * * * *

UNITED STATES PATENT AND TRADEMARK OFFICE
CERTIFICATE OF CORRECTION

PATENT NO. : 5,451,398
DATED : September 19, 1995
INVENTOR(S) : Joseph E. Vigh

It is certified that error appears in the above-indentified patent and that said Letters Patent is hereby corrected as shown below:

Column 5, line 26, second equation; delete

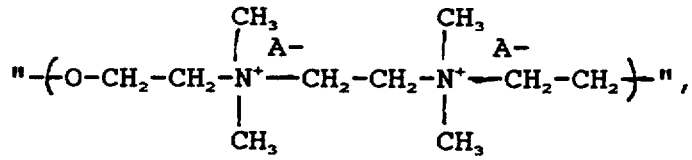

and insert in place thereof

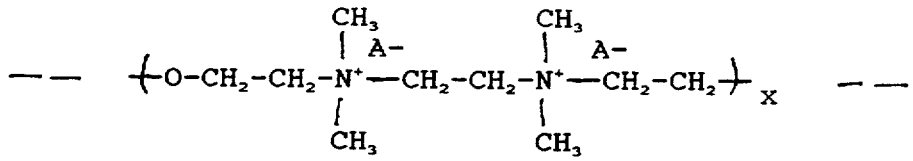

Column 13, line 5, claim 12; delete "and" and insert in place thereof --including--

Signed and Sealed this

Eleventh Day of March, 1997

Attest:

BRUCE LEHMAN

Attesting Officer  Commissioner of Patents and Trademarks